United States Patent [19]

Neuhaus

[11] Patent Number: Plant 7,310

[45] Date of Patent: Aug. 28, 1990

[54] POINSETTIA PLANT '15-84'

[75] Inventor: Wilhelm Neuhaus, Duisburg, Fed. Rep. of Germany

[73] Assignee: Paul Ecke Ranch, Inc., Encinitas, Calif.

[21] Appl. No.: 266,902

[22] Filed: Nov. 3, 1988

[51] Int. Cl.[5] ..... A01H 5/00

[52] U.S. Cl. ..... Plt./86

[58] Field of Search ..... Plt./86

*Primary Examiner*—James R. Feyrer

*Attorney, Agent, or Firm*—Arnold, White & Durkee

[57] ABSTRACT

Described is a new Poinsettia cultivar, '15-84', having large pink flower bracts. '15-84' is a vigorous, self-branching Poinsettia of medium height, with short petioles which cause the bracts to be tightly clustered around the cyathia. '15-84' is a sport of the poinsettia cultivar described in U.S. Plant Pat. No. 5,492.

1 Drawing Sheet

BACKGROUND OF THE INVENTION

'15-84' is a vigorous, self-branching Poinsettia of medium height and large pink flower bracts. The bract petioles are short causing the bracts to be tightly clustered around the cyathia. It has self-branching traits which make it desirable for branched plant production. '15-84' can be flowered in a relatively cool greenhouse, making it economical to grow commercially.

This new Poinsettia cultivar originated as a color sport of the red bracted cultivar described in U.S. Plant Pat. No. 5,492, in a greenhouse in Duisburg, West Germany. This pink sport has all the self-branching traits and other desirable growth characteristic of the cultivar of U.S. Plant Pat. No. 5,492. After selection, vegetatively reproduction of this plant by stem cuttings for test purposes in Duisburg, West Germany, and clones of the plant were subjected to successive generations of vegetative propagation which demonstrated that its pink bract coloration and other distinctive characteristics hold true from generation to generation.

DESCRIPTION OF THE PHOTOGRAPHS

'15-84' is illustrated in the accompanying color photographs. The upper photo is a side view of typical branched plant in full flower. The lower photo is a top view of a plant showing flower and bract formation.

DESCRIPTION OF THE PLANT

The following is a detailed description of this new Poinsettia as observed in Encinitas, Calif., during December, 1987. Observations were recorded from flowering plants, grown as 3 unpinched plants per pot. The pot was 14 cm. in diameter and 11 cm. in height. Color designations were compared to the 1986 edition of R.H.S. Colour Chart, first published in 1966 by The Royal Horticultural Society, London, England.

THE PLANT

Origin: Sport of the cultivar of U.S. Plant Pat. No. 5,492.

Classification:

*Botanic.*—*Europhobia pulcherrima* Willd.

*Common name.*—Poinsettia.

*Cultivar name.*—'15-84'.

Form: Shrub.

Height: Medium.

Growth habit: As a single stemmed plant, upright and vigorous. In full flower, the stem is terminated by a large inflorescence, with several smaller flowering side shoots lower on the stem. Observation of 3 plants in a pot with an overall height of 44 cm. and an overall width of 46 cm. were made. The bract diameter of individual flowers was 28 cm.

Branching: Branching can be enhanced by removal of the stem tip. Then, several flowering branches with equal vigor may develop on a single plant.

Growth rate: Very fast. Rooting of stem cuttings occurs in 12–18 days under intermittent mist. The plant will flower in about ten weeks under continuous long night conditions and night temperatures of about 16–18 degrees C.

Foliage: The foliage is clean and uniformly green from bottom to top of the plant. The leaves are of medium size, leaf blades typically being about 15–17 cm. long and about 9–10 cm. wide with leaf petioles about 5–6 cm. long.

Leaf shape: Typical leaves are ovate with obtuse bases and acuminate tips. Leaf margins are mostly entire with some modest lobing and undulation.

Color:

*Upper side.*—Darker than RHS 147A.

*Under side.*—Between RHS 137B an RHS 137C.

Retention: The foliage retention is good even under low light intensities in the consumer's home.

Bracts: Generally there are 21–24 pink bracts of various sizes subtending the cyathia. The primary bracts have blades typically 13–15 cm. long and 8–10 cm. wide with petioles about 2 cm. long.

Shape: Bracts are mostly ovate with acute bases and acuminate tips. Primary bracts are mostly entire; some with modest lobing on either side of the bract.

Color:

*Upper side.*—Pink, near RHS 51B.

*Under side.*—Near RHS 54C. The veining color, seen principally in the mid vein, is yellow-green (near RHS 154C). The pink bract color (near RHS 51B) varies in intensity with age of bract, being more intense in the newer, more recently expanded bracts, and fading in the older, more mature bracts. Bract color may not be uniform across the surface, fading towards the margins, especially in the lower, more mature bracts.

Cyathia: Generally, 18–21 cyathia (flowers) are present when the plant is in "full bloom". Each cyathium is about 7–8 mm long and about 5–6 mm wide, green in color and fading to yellow toward the distal end, but then fringed with red at the distal end. Usually, two bright yellow nectar cups protrude from the side of the cyathium. The flower pedicel is also green and about 6–7 mm in length. The anthers protruding from the cyathia are reddish.

What is claimed is:

1. A new and distinct Poinsettia cultivar, substantially as herein shown and described, distinguished by its large, pink flower bracts and vigorous, self-branching growth characteristics.

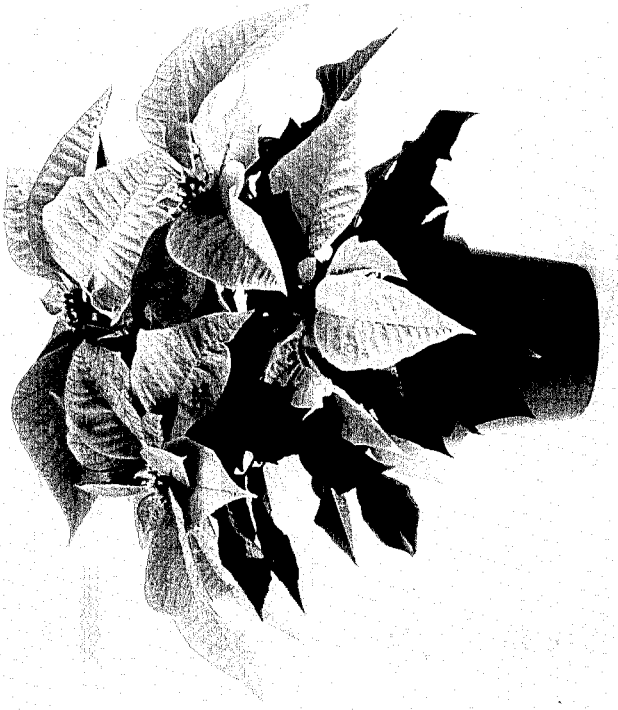
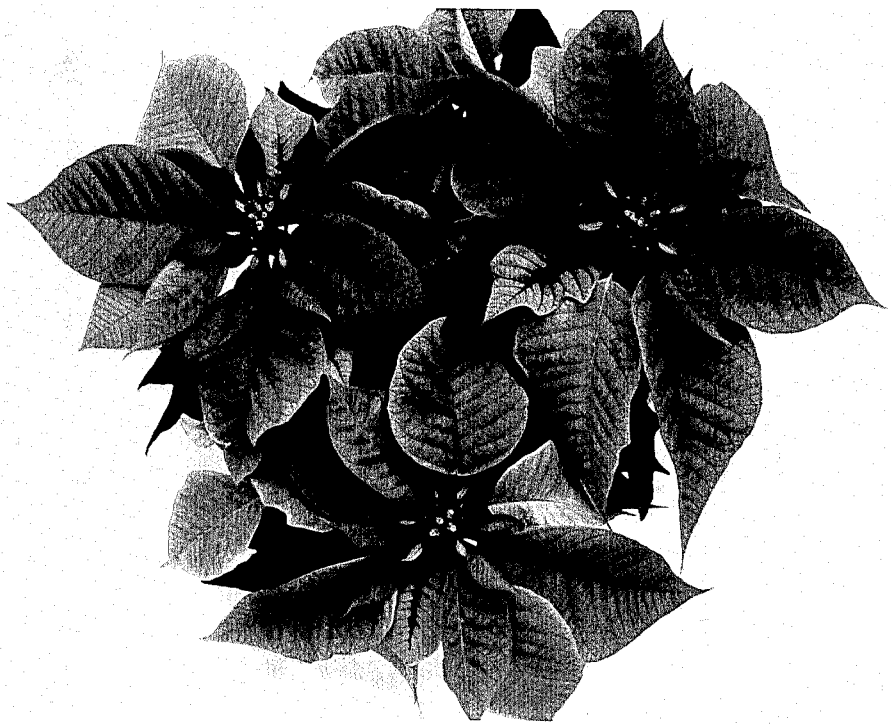

* * * * *